US010610596B2

(12) United States Patent
Genin

(10) Patent No.: US 10,610,596 B2
(45) **Date of Patent: *Apr. 7, 2020**

(54) METHODS OF MAKING SOLID VACCINE COMPOSITIONS HAVING REDUCED FOAMING

(71) Applicant: Abic Biological Laboratories Ltd., Beit Shemesh (IL)

(72) Inventor: Noel Yves Henri Jean Genin, Saint Genis les Ollieres (FR)

(73) Assignee: Abic Biological Laboratories Ltd., Beit Shemesh (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/256,463

(22) Filed: Jan. 24, 2019

(65) Prior Publication Data

US 2019/0151451 A1 May 23, 2019

Related U.S. Application Data

(60) Continuation of application No. 16/125,911, filed on Sep. 10, 2018, now Pat. No. 10,213,509, which is a division of application No. 14/880,145, filed on Oct. 9, 2015, now Pat. No. 10,188,734.

(60) Provisional application No. 62/062,180, filed on Oct. 10, 2014.

(51) Int. Cl.

| | |
|---|---|
| ***A61K 47/26*** | (2006.01) |
| ***A61K 9/46*** | (2006.01) |
| ***A61K 9/00*** | (2006.01) |
| ***A61K 9/20*** | (2006.01) |
| ***A61K 39/00*** | (2006.01) |
| ***A61K 39/12*** | (2006.01) |
| ***A61K 39/17*** | (2006.01) |
| ***A61K 39/215*** | (2006.01) |
| ***A61K 39/255*** | (2006.01) |
| ***A61K 39/275*** | (2006.01) |

(52) U.S. Cl.

CPC ............ *A61K 47/26* (2013.01); *A61K 9/0007* (2013.01); *A61K 9/0056* (2013.01); *A61K 9/2009* (2013.01); *A61K 9/2013* (2013.01); *A61K 9/2018* (2013.01); *A61K 9/2063* (2013.01); *A61K 39/00* (2013.01); *A61K 39/12* (2013.01); *A61K 39/17* (2013.01); *A61K 39/215* (2013.01); *A61K 39/255* (2013.01); *A61K 39/275* (2013.01); *A61K 2039/5252* (2013.01); *A61K 2039/552* (2013.01); *C12N 2760/18134* (2013.01); *C12N 2770/20034* (2013.01)

(58) Field of Classification Search

None

See application file for complete search history.

(56) References Cited

U.S. PATENT DOCUMENTS

| | | | |
|---|---|---|---|
| 4,710,378 | A | 12/1987 | Ohtomo et al. |
| 9,839,613 | B2 | 12/2017 | Qiao et al. |
| 2003/0026813 | A1 | 2/2003 | Gallili et al. |
| 2006/0246089 | A1 | 11/2006 | Wu et al. |
| 2012/0087944 | A1 | 4/2012 | Tian et al. |

FOREIGN PATENT DOCUMENTS

| | | | |
|---|---|---|---|
| CN | 1528458 | A | 9/2004 |
| CN | 1261161 | C | 6/2006 |
| CN | 102160856 | A | 8/2011 |
| WO | 01/13896 | A1 | 3/2001 |
| WO | 02/067846 | A2 | 9/2002 |
| WO | 2004026336 | A1 | 4/2004 |
| WO | 2007/014073 | A2 | 2/2007 |
| WO | 2007132480 | A2 | 11/2007 |

OTHER PUBLICATIONS

Perozo, et al., Avian Pathliogy (2008) 37(3):237-245.
Corbaine, et al. Vaccine (2007) 25:8306-8317.
Zhang, et al., Life Sciences Journal (2009) 6(1):13-17.
Umino, et al., Journal of General Virology (1990) 71:1199-1203.
Matthijs, et al., Avian Diseases (2008) 52(3):461-466.
R.D. Jangle, et al., Vacuum Form Drying: An Alternative to Lyophilization for Biomolecule Preservation, Indian Journal of Pharmaceutical Sciences (2012) 74(2):91-100.
Jai K. Kaushik, et al., Thermal Stability of Proteins in Aqueous Polyol Solutions: Role of the Surface Tension of Water in the Stabilizing Effect of Polyols, J. Phys. Chem B (1998) vol. 102, p. 7058-7066.
Applicant Confidential, Trade Secret and/or Proprietary Material That Is Not Open to Public and Is Not to Be Scanned.

*Primary Examiner* — Nicole Kinsey White
(74) *Attorney, Agent, or Firm* — Klarquist Sparkman, LLP

(57) ABSTRACT

Disclosed and claimed are methods for making solid vaccine compositions that have reduced foaming when mixed with liquid diluent. The methods include mixing an effective amount of a foam controlling agent with at least one anhydrous antigenic component, a stabilizer, and an effervescent agent. The foam controlling agent is a sugar alcohol, such as mannitol. The effective amount of sugar alcohol is about 15% to about 40% by weight of the solid vaccine composition. And, upon adding a diluent to the solid vaccine composition, the effervescent agent reacts to form gas in situ, and foam resulting from the gas is reduced.

46 Claims, 4 Drawing Sheets

METHODS OF MAKING SOLID VACCINE COMPOSITIONS HAVING REDUCED FOAMING

CROSS-REFERENCE TO RELATED APPLICATIONS

This application is a continuation of U.S. application Ser. No. 16/125,911, filed Sep. 10, 2018, now U.S. Pat. No. 10,213,509, which application is a divisional of U.S. application Ser. No. 14/880,145, filed Oct. 9, 2015, now U.S. Pat. No. 10,188,734, which claims priority to U.S. Provisional Application Ser. No. 62/062,180, filed Oct. 10, 2014, the disclosure of which is incorporated by reference in its entirety.

Each of these applications, patents, and each document cited in this text, and each of the documents cited in each of these applications, patents, and documents ("application cited documents"), and each document referenced or cited in the application cited documents, either in the text or during the prosecution of the applications and patents thereof, as well as all arguments in support of patentability advanced during prosecution thereof, are hereby incorporated herein by reference.

FIELD OF THE INVENTION

The present invention relates to a stable compacted, compressed vaccine composition comprising a compressed vaccine composition comprising at least one lyophilized antigenic component and a foam controlling agent, and a process of making thereof. This stable dense vaccine composition retains titer stability and while further providing complete dissolution in a diluent with minimum foaming. A method for vaccinating a subject using the stable vaccine composition is also provided.

BACKGROUND OF THE INVENTION

PCT Publication No. WO 99/21579 (Seager, et al.) discloses a fast dispersing composition for a veterinary vaccine that is freeze dried and loosely compacted. U.S. Pat. No. 5,587,180 (Allen Jr. et al) describes a process for making a particulate support matrix for a rapidly dissolving tablet. U.S. Pat. No. 5,336,666 (Neway et al.) discloses a freeze dried liquid vaccine that may form a tablet to be reconstituted in liquid form.

A disadvantage to current vaccine preparations is that they contain stabilizers susceptible to foaming when mixed in diluent, causing excessive foaming of the solution after dissolution of the composition which also causes problems for the user in containing the solution in the container its dissolved in. Overflow of the solution from the container due to foaming can result in loss of product and increased exposure of the vaccine to the user.

SUMMARY OF THE INVENTION

Accordingly, it is an object of the invention to provide a stable vaccine composition and method of immunizing accomplished by simply dissolving a solid, stable form of an anhydrous vaccine in a diluent with minimum foaming and minimum loss of antigenic activity.

A further object of the invention is to provide a lyophilized live or inactivated vaccine which is compacted, compressed or tableted as a dense stable solid that will retain its potential immunizing capacity during preparation and for the duration required for a pharmaceutically acceptable period of time and can be dissolved in diluent with minimum foaming.

Another object of the invention is to provide a vaccine composition and method of immunizing with greater flexibility in the vaccinations that can be formulated and uses thereof.

A further object of the invention is to provide a vaccine composition and method of immunizing which reduces the need for excess vaccine material needed to compensate for the inherent inaccuracies in the titer caused by over-foaming and loss of product during dissolution.

Another object of the invention is to provide a vaccine composition and method of immunizing which facilitates avian mass immunization.

These and other objects may be achieved by the present invention which relates to a stable vaccine composition comprising at least one pre-titrated lyophilized antigenic component, and foam-controlling agent, wherein the vaccine composition is in the form of a compressed composition. In addition, the present invention also provides a method of immunizing a subject against a disease comprising the steps of: dissolving the compressed vaccine composition containing the foam controlling agent in a pharmaceutically acceptable diluent to form a solution; and administering the resulting solution to the subject in an amount effective to immunize the subject against the disease.

The invention in its particular features will become more apparent from the following detailed description considered with reference to the accompanying examples. The following description will continue to discuss the problems and solutions offered by the present invention as they pertain to veterinary applications.

It is noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is further noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

DETAILED DESCRIPTION OF THE INVENTION

Figure 1:
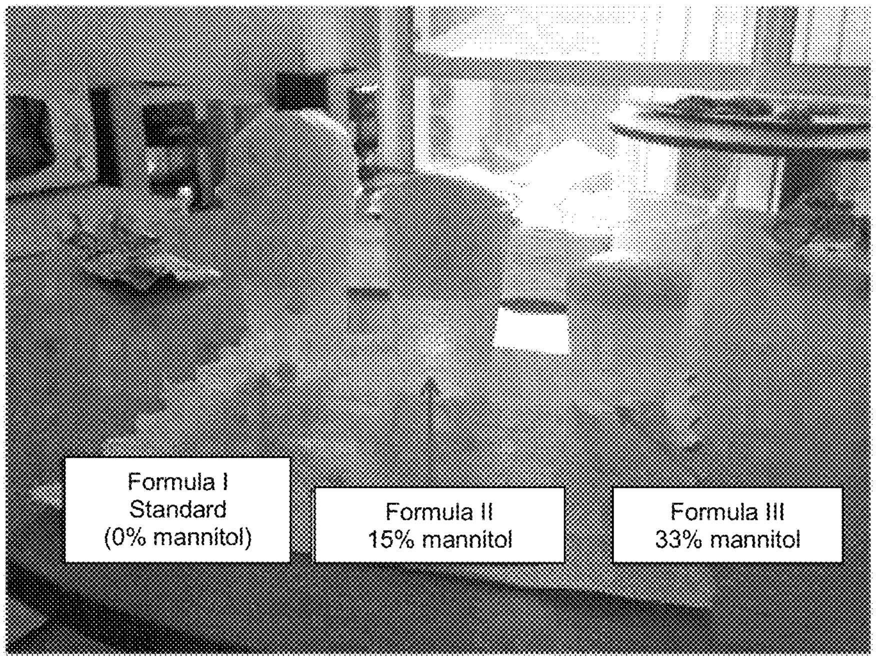
FIG. 1 shows containers containing Formula I (control containing 0% mannitol), Formula II (containing 15% mannitol), and Formula III, (containing 33% mannitol).

The invention provides a stable compressed vaccine composition comprising at least one lyophilized antigenic component, and a foam controlling agent.

In an embodiment of the invention, the vaccine composition dissolves completely and rapidly in a diluent.

In an embodiment of the invention, the vaccine composition is in the form of a hard tablet, a caplet, a granulation, a sprinkle, a pellet, a bead, a pill, or a lyophilized cake.

In an embodiment of the invention, the vaccine composition comprises a dissolution agent which is an effervescent agent or pair of agents.

In an embodiment of the invention, the vaccine composition comprises a dissolution agent comprises a pair of effervescent agents.

In an embodiment of the invention, the vaccine composition comprises as effervescent pair comprising a salt and an acid e.g. citric acid and the salt is a bicarbonate.

In an embodiment of the invention, the vaccine composition comprises a foam controlling agent comprising about 25% to 40% by weight of the composition.

In an embodiment of the invention, the vaccine composition comprises a dissolution agent comprising up to about 60% by weight of the composition.

In an embodiment of the invention, the vaccine composition comprises a dissolution agent comprising up to about 35% by weight of the composition.

In an embodiment of the invention, the vaccine composition comprises a lyophilized antigenic component comprising up to 90% by weight of the composition.

In an embodiment of the invention, the vaccine composition comprises a lyophilized antigenic component comprising up to 80% by weight of the composition.

In an embodiment of the invention, the vaccine composition is characterized by complete dissolution between about 90 and 700 seconds upon contact with a diluent.

In an embodiment of the invention, the stability of the composition is characterized by a loss of titer no greater than the difference shown in the examples.

In an embodiment of the invention, the vaccine composition comprises a foam controlling agent that is a sugar alcohol.

In an embodiment of the invention, the vaccine composition comprises a foam controlling agent that is xylitol, mannitol and sorbitol.

In an embodiment of the invention, the vaccine composition comprises a foam controlling agent that is mannitol.

In an embodiment of the invention, the vaccine composition comprises an antigenic component that is IB88 or IBH120.

In an embodiment of the invention, the vaccine composition has a friability of less than about 2%.

In an embodiment of the invention, the vaccine composition comprises a live virus selected from the group consisting of: Newcastle Disease virus, Infectious Bursal Disease virus, fowl pox virus, Laryngotracheitis virus, Infectious Bronchitis of poultry virus, sheep pox virus, Rinderpest virus, or an admixture of one or more of the foregoing, whether naturally occurring, recombinant or modified.

In an embodiment of the invention, the vaccine composition comprises an antigenic component selected from the group consisting of; anthrax bacilli, *Salmonella* S.P.P. *E. coli*, or an admixture of one or more of the forgoing, whether naturally occurring or recombinant or modified.

In an embodiment of the invention, the vaccine composition comprises an antigenic component that is a live virus and the composition further comprises neutralizing antibodies against the virus.

In an embodiment of the invention, a method of vaccinating a subject against a disease comprising the steps of: dissolving the vaccine composition of the invention which provides protection against such disease with a diluent to form a solution; and administering the resulting solution to the subject in an amount effective to immunize the subject against the disease.

In an embodiment of the invention, a method of vaccinating a subject wherein the dissolving step is further characterized by complete dissolution of the vaccine composition.

In an embodiment of the invention, a method of vaccinating a subject dissolution occurs between about 90 and 700 seconds upon contact with a diluent wherein the administering step comprises spraying the subject with an aerosol formed from the solution.

In an embodiment of the invention, a process of making a stable compressed rapidly dissolving vaccine composition of the invention comprising the steps of: lyophilizing, at least one antigenic component; mixing the lyophilized antigenic component and foam controlling agent; and compressing the mixture of the lyophilized antigenic component and foam controlling agent with at least one dissolution agent to form a stable compressed rapidly dissolving vaccine composition.

Other embodiments of the invention will be further described by the following numbered paragraphs:

1. A process for reducing the foaming of a solid vaccine composition when mixed with liquid diluent, wherein the composition comprises:

(i) at least one anhydrous antigenic component comprising a stabilizer susceptible to foaming; wherein the process comprises:

(a) adding an effective amount of a sugar alcohol to the solid vaccine composition.

2. A process according to paragraph 1, wherein the process further comprises:

(b) compressing the solid vaccine composition to form a stable compressed vaccine composition.

3. A process according to paragraph 1 or 2, wherein the anhydrous antigenic component is lyophilized or dried.

4. A process according to any one of paragraphs 1 to 3, wherein the stabilizer comprises one or more amino acid of salts thereof, protein or salts thereof, albumin, gelatin, or combinations thereof.

5. A process according to any one of paragraphs 1 to 4, wherein antigenic component is newcastle disease virus, infectious bronchitis virus, fowl pox virus, avian encephalomyelitis virus, marek's disease virus, *Trichophyton verrucosum*, avian paramyxovirus, *mycobacterium* paratuberculosis, meleagrid herpesvirus, orf virus, or sheep pox virus.

6. A process according to any one of paragraphs 1 to 4, wherein the antigenic component is newcastle disease virus, or infectious bronchitis virus.

7. A process according to any one of paragraphs 1 to 6, wherein the composition is mixed by sonication, mechanical or chemical means.
8. A process according to any one of paragraphs 1 to 6, wherein the composition is mixed by sonication or mechanical means.
9. A process according to any one of paragraphs 1 to 6, wherein the composition is mixed by chemical means.
10. A process according to paragraph 9, wherein the chemical means is an effervescent reaction.
11. A process according to any one of paragraphs 1 to 10, wherein the composition further comprises a dissolution agent.
12. A process according to paragraph 11, wherein the dissolution agent is an effervescent agent or pair of effervescent agents.
13. A process according to paragraph 11, wherein the dissolution agent comprises a pair of effervescent agents.
14. A process according to paragraph 13, wherein the pair of effervescent agents comprises a salt and an acid.
15. A process according to paragraph 14, wherein the acid is citric acid, tartaric acid, malic acid, fumaric acid, adipic acid, succinic acid, acid anhydrides or mixtures thereof.
16. A process according to paragraph 14, wherein the salt is carbonate salts, bicarbonate salts, sesquicarbonate salts, or mixtures thereof.
17. A process according to any one of paragraphs 1 to 16, wherein the effective amount of sugar alcohol is about 10% to 40% by weight of the composition.
18. A process according to any one of paragraphs 1 to 16, wherein the effective amount of sugar alcohol is about 10% to 35% by weight of the composition.
19. A process according to any one of paragraphs 1 to 16, wherein the effective amount of sugar alcohol is about 15% to 35% by weight of the composition.
20. A process according to any one of paragraphs 11 to 19, wherein the dissolution agent is tap to about 60% by weight of the composition.
21. A process according to any one of paragraphs 11 to 19, wherein the dissolution agent is about 30% to about 60% by weight of the composition.
22. A process according to any one of paragraphs 1 to 21, wherein the anhydrous antigenic component is about 20% to about 50% by weight of the composition.
23. A process according to any one of paragraphs 1 to 21, wherein anhydrous antigenic component is up about 20% to about 40% by weight of the composition.
24. A process according to any one of paragraphs 1 to 23, wherein the solid vaccine composition is characterized b complete dissolution of the composition in the diluent between about 60 and 700 seconds upon contact with the diluent.
25. A process according to any one of paragraphs 1 to 24 wherein the solid vaccine composition is characterized by complete dissolution of the composition in the diluent between about 60 and 300 seconds upon contact with the diluent.
26. A process according to any one of paragraphs 1 to 25, wherein the foaming of the solid vaccine composition is reduced relative to the foaming of the composition in the absence of the sugar alcohol.
27. A process according to any one of paragraphs 1 to 26, wherein the sugar alcohol is xylitol, mannitol or sorbitol or a mixture thereof.

28. A stable vaccine composition comprising:
   i) at least one anhydrous antigenic component comprising a stabilizer susceptible to foaming when the composition is mixed with liquid diluent; and
   ii) an effective amount of a foam controlling agent which is a sugar alcohol.
29. A stable vaccine composition according to paragraph 28, wherein the anhydrous antigenic component is lyophilized or dried.
30. A stable vaccine composition according to paragraph 28 or 29, wherein the vaccine composition is compressed into a tablet.
31. A stable vaccine composition according to any one of paragraphs 28 to 30, wherein the stabilizer comprises one or more amino acid or salts thereof, protein or salts thereof, albumin, gelatin, or combinations thereof.
32. A stable vaccine composition according to any one of paragraphs 28 to 30, wherein the stabilizer is an amino acid or salts thereof proteins or salts thereof, or combinations thereof.
33. A stable vaccine composition according to any one of paragraphs 28 to 32, wherein antigenic component is newcastle disease virus, infectious bronchitis virus, fowl pox virus, avian encephalomyelitis virus, marek's disease virus, *Trichophyton verrucosum*, avian paramyxovirus, *mycobacterium* paratuberculosis, meleagrid herpesvirus, orf virus, or sheep pox virus.
34. A stable vaccine composition according to any one of paragraphs 28 to 33, wherein the antigenic component is Infectious Bronchitis virus strain CR88121, Infectious Bronchitis virus strain H120 or Newcastle Disease virus strain VG/GA.
35. A stable vaccine composition according to any one of paragraphs 28 to 34, further comprising a dissolution agent.
36. A stable vaccine composition according to paragraph 35, wherein the dissolution agent is an effervescent agent or pair of effervescent agents.
37. A stable vaccine composition according to paragraph 35, wherein the dissolution agent comprises a pair of effervescent agents.
38. A stable vaccine composition according to paragraph 36, wherein the effervescent pair comprises a salt and an acid.
39. A stable vaccine composition according to paragraph 28, wherein the effective amount of sugar alcohol is about 10% to 40% by, weight of the composition.
40. A stable vaccine composition according to any one of paragraphs 28 to 39, wherein the effective amount of sugar alcohol is about 10% to 35% by weight of the composition.
41. A stable vaccine composition according to any one of paragraphs 28 to 39, wherein the effective amount of sugar alcohol is about 15% to 35% by weight of the composition.
42. A stable vaccine composition according to any one or paragraphs 35 to 41, wherein the dissolution agent is up to about 60% by weight of the composition.
43. A stable vaccine; composition according to any one of paragraphs 35 to 41, wherein the dissolution agent is about 30% to about 60% by weight of the composition.
44. A stable vaccine composition according to any one of paragraphs 28 to 43, wherein the lyophilized antigenic component is up to 90% by weight of the composition.
45. A stable vaccine composition according to any one of paragraphs 28 to 43, wherein the lyophilized antigenic component is up to 80% by weight of the composition.
46. A stable vaccine composition according to any one of paragraphs 28 to 45, wherein the composition is characterized by complete dissolution of the composition in the diluent between about 60 and 700 seconds upon contact with the diluent.

47. A stable vaccine composition according to any one of paragraphs 28 to 46, wherein the composition is characterized by reduction in foaming of the composition when in contact with the diluent relative to the foaming of the composition in the absence of the sugar alcohol.

48. A stable vaccine composition according to any one of paragraphs 28 to 47, wherein the sugar alcohol is xylitol, mannitol, sorbitol, or a mixture thereof.

49. A stable vaccine composition according to any one of paragraphs 28 to 47, wherein the sugar alcohol is mannitol.

50. A stable vaccine composition according to paragraph 35, wherein composition has a friability of less than about 2%.

51. A stable vaccine composition according to any one of paragraphs 28 to 50, wherein the antigenic component is a live virus and the composition further comprises neutralizing antibodies against the virus.

52. A stable vaccine composition according to any one of paragraphs 28 to 51, wherein the composition is stable at 5° C. in anhydrous conditions for at least 9 months.

53. A stable vaccine composition according to any one of formulations 2, 4, 6, II, III, B, D or E shown in the examples.

52. A stable vaccine composition according to any one of paragraphs 28 to 53, wherein the foam is reduced by about 50%, by about 60% or by about 80% than the same composition without the sugar alcohol 56. A method of vaccinating a subject against a disease comprising the steps of:

(a) dissolving the vaccine composition of any one of paragraphs 28 to 55, which provides protection against such disease, with a diluent to form a solution; and (b) administering the resulting solution to the subject in an amount effective to the subject against the disease.

57. The method of paragraph 54, wherein the administering step comprises spraying the subject with an aerosol formed from the solution.

The compacted, compressed and hard tablets of the vaccine composition can be made on an instrumented MANESTY F3 Single punch 12 mm Flat Beveled or 6 mm standard concave punches. The vaccine composition in the form of a hard tablet can be made at a pressures of a maximum of 4 tonnes. The tablets can be tested for hardness on a ERWEKA Tablet Hardness Tester Model TBH20 as described above, and were all found to have a hardness greater than 3.0 seD. The classic tablet normally associated with therapeutic agents is understood to be such a "tablet". However, it is understood that any compacted or compressed dense form is intended, including those having less frequent use in the pharmaceutical field. For example, large "briquettes" would be suitable should the final application require a large volume of material.

Specifically, tablet fillers are substances that compromise the bulk of the tablet and primarily act as a carrier. Typical tablet fillers include, but are not limited to, calcium sulfate, calcium phosphate, calcium carbonate, starch, modified starches (carboxymethyl starch, etc.), microcrystalline cellulose, lactose, sucrose, dextrose mannitol and sorbiol. Tablet filler levels are from about 0% to 90% by weight of the tablet.

Binders act as the "glue" which holds powders together to form granules. Binders include, but are not limited to, natural polymers such as starches or gums acacia, tragacanth and gelatin or synthetic polymers such as PVP and methyl-, ethyl- and hydroxypropylcellulose. Binder levels are from about 0% to 20% by weight of the composition.

Dissolution aids promote dissolution of the vaccine composition. Typical examples include, but are not limited to effervescent agents, disintegrates, surfactants and solubilizers.

Disintegrants cause compressed tablets to break apart. Typical examples include, but are not limited to, starch, microcrystalline cellulose, purified wool starch, alginic acid, sodium starch glycolate guar gum, crosslinked polyvinyl pyrolidone (PVP), ion exchange resin and celluloses such as methyl-, croscarmellose sodium, sodium carboxymethyl- and hydroxypropylmethyl-. Dissolution agent levels are from about 1% to 95% by weight of the composition.

Lubricants reduce friction between the material to be compressed and die wall during compression and ejection. Most lubricants are water insoluble and include stearates (magnesium, calcium and sodium), stearic acid, talc and waxes. Water soluble lubricants include PEGs, sodium benzoate, sodium oleate, sodium acetate, sodium lauryl sulfate and magnesium lauryl sulfate. Lubricant levels are from about 0% to 5% by weight of the composition.

Colorants are added to help identify types of vaccine formulations such as in the form of tablets for aesthetic an functional purposes, for example and not as limitation to the present invention, the dyes disclosed in Examples A through D taken from Israeli Patent No. 46189. Colorant levels are from about <1% of the formulation. In an embodiment, the composition of the present invention is a hard tablet prepared having an effervescent agent as a dissolution aid. As those skilled in art appreciate, the effervescent tablet must contain a basic component and an acidic component, such as an effervescent pair, so that upon dissolution appropriate reactions occur to generate carbon dioxide and carbonic acid. Suitable effervescent components include the carbonate family of basic compounds and inorganic or organic acidic compounds. Among the carbonate family of basic compounds, preferred effervescent agents for use in the compositions of the present invention are sodium carbonate, sodium bicarbonate, glycine carbonate, potassium carbonate, potassium bicarbonate, potassium dihydrogencitrate, and calcium carbonate. A most preferred basic compound is sodium bicarbonate. Preferred acidic components for use in the compositions of the present invention are citric acid, adipic acid, tartaric acid, maleic acid, boric acid, benzoic acid, hydroxybenzoic acid, methoxy benzoic acid, mandelic acid, malonic acid, lactic acid, pyruvic acid, glutaric acid, aspartic acid, hydrochloric acid, oxalic acid, salicylic acid, succinic acid, and acetic acid. A most preferred acidic effervescent component is citric acid. Also, the acid component can comprise citric acid, tartaric acid, malic acid, fumaric acid, adipic acid, succinic acid, acid anhydrides or mixtures thereof.

In addition to the basic and acidic effervescent tablet ingredients described above, the tablet composition of the present invention may also contain other excipients conventionally employed.

DEFINITIONS

Terms used herein wilt have their customary meaning in the art unless specified otherwise.

The term "antigenic component" or "antigen" as used herein is a substance that is recognized by the immune system and induces an immune response. The substance may comprise a whole organism, killed, attenuated or live; a subunit or portion of an organism; a recombinant vector containing an insert with antigenic properties; a nucleic acid piece or fragment capable of inducing an immune response upon presentation to a host animal; a protein, a polypeptide, a peptide, a glycoprotein, an epitope, a hapten, a carbohydrate, a sugar, or any combination thereof. Alternatively, the antigen may comprise a toxin or antitoxin. A similar term used interchangeably in this context is "immunogen" or "antigenic".

The term "compacted" as used herein refers to a vaccine composition having a density greater than 1.0 g/cc, but no measurable hardness as measured in Strong-Cobb Units (SCU) and tested for hardness on a ERWEKA Tablet Hardness Tester Model TBH20.

The term "compressed" as used herein refers to a vaccine composition having a hardness of at least 2.0 SCU.

The term "hard tablet" as used herein refers to a vaccine composition in the form of a tablet or other dense form having a hardness of at least 3.0 SCU.

The term "completely dissolved" as used herein is understood to mean that no soluble component is left undissolved.

The term "rapidly disintegrated" or "rapidly dissolved" as used herein is understood to mean that disintegration or dissolution is complete within approximately a few minutes or less when a large volume of water is employed for small volume of compressed lyophilized vaccine composition e.g. 100 ml of water for a 400 mg effervescent tablet. The time is increased where the volumes of diluent are comparably decreased. Thus the same tablet might require 70 seconds with a volume of water of 10 ml, and 8O seconds in 2 ml of water.

The term, "disintegration time" or "dissolution time" as used herein is the time taken for dissolution or disintegration of a tablet when mixed in a measured quantity of water at room temperature.

The term "stable" as used herein is understood to mean that the compositions of the present invention will maintain their (potential) immunizing capacity during preparation and for the duration required for shelf life of a commercial vaccine.

The term "excipient" as used herein refers to a term for diluents or vehicles used in the formulation or the vaccine composition. Excipients can include: diluents or fillers, binders or adhesives, dissolution aids, lubricants, antiadherents, glidants or flow promoters, colors, flavors, sweeteners and adsorbents.

The term "stabiliser" as used herein is chemical compounds used to stabilize antigenic material during lower temperature storage or lyophilisation. Examples of such stabilizers include amino acids, such as alanine, arginine, aspartic acid, cystine, glutamic acid, glycine, histidine, hydroxy proline, isoleucine, leucine, lysine, methionine, phenyl alanine, proline, serine, threonine, tyrosine, and valine; amino acids salts thereof such as L-arginine hydrochoride salt and glutamic acid alkali metal salt such as monosodium glutamate and monopotassium glutamate; proteins, or salts thereof, such as protein hydrolysate, bovine protein, mouse serum protein, calf serum protein, yeast protein, chicken protein, egg protein; albumin such as bovine albumin and ovalbumin, gelatin, and hydrolysed gelatin The stabilizer also includes a monosaccharide, e.g., sorbitol, or a disaccharide, e.g., sucrose, lactose, or maltose. Sucrose is preferred.

The term "mixed" as used herein means mixing a substance by sonication, mechanical or chemical means. Examples of mechanical mixing include stirring, shaking, magnetic stirring, and forcing the substance through a suitable syringe. Examples of chemical mixing include an effervescent reaction causing in-situ gas formation (via chemical reaction of one or more ingredients, including formation of carbon dioxide ($CO_2$ gas) sufficient to cause a mixing action as the resultant release of gas bubbles pass through the liquid to the surface.

The antigenic component as defined herein can comprise live attenuated pathogens, such a live attenuated viruses, bacteria, fungi, or parasites. However, an active antigenic component can also comprise killed viruses, recombinant heterologous immunogens, antigens, antigenic subunits (e.g. proteins, polypeptides, peptides, epitopes, haptens) or epitopes of immunogens or antigens derived from or originating from one or more pathogens described herein, which can be expressed from viral vectors, bacterial vectors, plasmid vectors, and the like.

The active antigenic component of the present invention can comprise one or more immunogens selected from a canine pathogen including, but not limited to, rabies virus, canine adenovirus type 2 (CAV2), canine herpesvirus (CHV), canine parvovirus (CPV), canine coronavirus, *Leptospira canicola, Leptospira icterohaemorragiae, Leptospira grippotyphosa, Borrelia burgdorferi, Bordetella bronchiseptica* and the like, including combinations thereof. The active antigenic component can include the HA, F, NP genes from the CDV, the capsid gene from CPV, the spike, M, N genes from Canine coronavirus, the HN and F genes from cPi2, genes from *Lepiospira*, genes from *Bordetella*, genes from *Borrelia*, and the gB, gC and gD genes from the canine herpesvirus, among others. These components can be useful as antigenic compositions or vaccine compositions for protecting canines against disease caused by these pathogens.

Canine Adenovirus Type 2 (CAV2) is widespread and highly contagious to dogs, it produces symptoms resembling a cold. Generally the first signs of the contagious disease are fever, which usually subsides in one to two days. Affected dogs may have tonsillitis, abdominal tenderness, enlarged liver, vomiting and diarrhea. Acute disease is normally fatal. CAV2 may be inactivated or attenuated and combined with the CDV (and/or cPi2) to produce a multivalent vaccine. Alternatively, immunogens or antigens of CAV2, or epitopes of CAV2 immunogens, such as capsid, matrix, or hexon proteins, can be used.

Canine Parvovirus (CPV) is a common intestinal virus which may cause vomiting, diarrhea, gastroenteritis, myocarditis and hepatitis in young dogs. It has been found to be widespread in dogs. CPV can be present in the antigenic compositions, suspensions, or solutions of the invention as inactivated, live attenuated, or CPV immunogens, antigens, or epitopes of CPV immunogens, such as the VP1, VP2 (capsid) gene products.

Other active antigenic component useful in the compositions and methods of the present invention can comprise one or more immunogens selected from avian pathogens including, but not limited to, *Salmonella typhimurium, Salmonella enteritidis*, Infectious Bronchitis virus (IBV), Newcastle Disease virus (NDV), egg drop syndrome virus (EDS), Infectious Bursal Disease virus (IBDV), turkey virus, avian influenza virus, Marek's disease virus, Herpesviruses such as infectious laryngotracheitis virus, avian infectious bronchitis virus, avian reovirus, poxviruses including avipox, fowlpox, canarypox, pigeonpox, quailpox, and dovepox, avian polyomavirus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus avian rotavirus, avian leukosis virus, avian musculoaponeurotic fibrosarcoma virus, avian myeloblastosis virus, avian myeloblastosis-associated virus, avian myelocytomatosis virus, avian sarcoma virus, avian spleen necrosis virus, and combinations thereof.

As to specific immunogens, the active antigenic components can also be the HN and F genes of Newcastle Disease Virus, the polyprotein and VP2 genes from infectious Bursal Disease Virus, the S and N genes from Infectious Bronchitis Virus and the gB and gD genes from Marek's Disease Virus. These components can be used as antigenic compositions or vaccine compositions for protecting avians against disease caused by these pathogens.

Alternatively, the active antigenic component comprises one or more immunogens from a feline pathogen such as, but not limited to, feline herpesvirus (FHV), feline calicivirus (FCV), feline leukemia virus (FeLV), feline infectious peritonitis virus, feline panleucopenia virus, feline immunodeficiency virus (FIV), rabies virus, and the like, and combinations thereof.

The active antigenic component can also include the gB, gC and gD genes from the Feline Herpesvirus, the env and gag/pro genes from the FeLV, the env gag/pol and tat genes from the FIV virus, the capsid gene from the Feline calicivirus, the S modified gene, M, and N gene from the Feline Infectious Peritonitis Virus, and the VP2 gene from the Feline parvovirus. These components can be useful as antigenic or vaccine compositions for protecting cats against disease caused by these pathogens.

The active antigenic component can comprise one or more immunogens from an equine pathogen, such as equine herpesvirus (type 1 or type 4), equine influenza virus, equine encephalomyelitis virus (EEV), tetanus, West Nile virus, and the like or combinations thereof. The active antigenic component can also include, the gB, gC, gD and Immediate-Early genes from Equine herpesvirus type 1, the gB, gC, gD and Immediate-Early genes from Equine herpesvirus type 4, the HA, NA, M and NP genes from Equine influenza virus, genes from Eastern Equine Encephalitis Virus, genes from Western Equine Encephalitis Virus, genes from Venezuelan Equine Encephalitis Virus, the prM-M-E genes from the West Nile Virus, and genes from Equine arteritis virus, but are not limited to these sequences. These components can be useful as antigenic compositions or vaccine compositions for protecting horses against disease caused by these pathogens.

The active antigenic component can comprise one or more immunogens from a bovine pathogen, such as rabies virus, bovine rotavirus, bovine parainfluenza virus type 3 (bCPI2-3), bovine coronavirus, bovine viral diarrhea virus (BVDV), foot and mouth disease virus (FMDV), bovine respiratory syncytial virus (BRSV), Infectious Bovine Rhinotracheitis virus (IBR), *Escherichia coli, Pasteurella multocido, Pasteurella haemolytica*, and the like and combinations thereof.

The active antigenic component can also be selected from the gB, gC, gD and Immediate Early genes from Bovine Herpesvirus type 1, the F and G genes from BRSV, the polyprotein, E1, E2 genes from BVDV, the HN and F genes from PI3 virus or genes from Rotavirus. These components can be useful as antigenic or vaccine compositions for protecting cattle against disease caused by these pathogens.

Further, the active antigenic component can comprise one or more immunogens from a porcine pathogen such as, but not limited to, swine influenza virus (SIV), porcine circovirus type 2 (PCV-2), porcine reproductive respiratory syndrome virus (PRRSV), pseudorabies virus (PRV), porcine parvovirus (PPV), hog cholera virus (HCV), FMDV, *Mycoplasma hyopneumoniae, Erysipelothrix rhusiopathiae, Pasteurella multocida, Bordetella bronchiseptica, Escherichia coli*, and the like, and combinations thereof.

The active antigenic component can also include the gB, gD and Immediate-Early genes from PRV, the HA, NA, M and NP genes from Swine influenza virus, the polyprotein, E1, E2 from Hog Cholera Virus, the ORF1 and ORF2 genes from PCV2 virus, the ORF3, ORF4, ORF5, ORF6, or ORF7 from PRRSV virus or genes from *Mycoplasma hyopneumoniae*. These components can be useful as antigenic compositions or vaccine compositions for protecting pigs against disease caused by these pathogens.

The active antigenic component can comprise sequences encoding a protein expressed in pathogens such as RNA or DNA viruses like HIV, HCV, HBV, HPV, EBV, HSV, CMV, HTLV, Hanta virus, Ebola virus, Marburg virus, Rift Valley fever virus, Lassa virus and influenza virus, hemorrhagic enteriditis virus (HEV), infectious rhinotracheitis virus (IBRV) among others. Such immunogens can be used advantageously as antigenic compositions or vaccine compositions to protecting subjects, such as humans, against disease caused by these pathogens.

The active antigenic component can also be, for example, from any one of the following pathogenic bacteria and their antigens: *Actinobacillus* species such as *Actinobacillus pleuropneumoniae, Bordetella pertussis, Bordetella parapertussis, Bordetella bronchiseptica, Bordetella avium, Chlamydia trachomatis, Chlamydia pneumoniae, Chlamydia psitiaci, Klebsiella species such as Klebsiella pneumoniae, Mycobacterium tuberculosis, Mycobacterium pseudotuberulosis, Mycobacterium pneumoniae*, Group A *Streptococcus, Streptococcus equi, Streptococcus pneumoniae, Streptococcus agalactiae, Streptococcus pyogenes, Streptococcus viridans, Neisseria gonorrhoeae, Erysipelothrix* species, Enterotoxigenic *Escherichia coli, Vibrio cholerae, Bacillus anthracis, Haemophilus influenzae, Haemophilus somnus, Haemophilus parasuis, Salmonella* species, *Salmonella agona, Salmonella blockley, Salmonella enteriditis, Salmonella hadar, Salmonella Heidelberg, Salmonella montevideo, Salmonella senfienberg, Salmonella cholerasuis, Rickettsia* species, *Helicobacter pylori, Helicobacter felis, Shigella* species, *Listeria* species, *Legionella pneumoniae, Pseudomonas* species, *Borrelia* species, *Borellia burgdorferi, Neisseria meningitides, Clostridium* species, *Clostridium difficile, Ureaplasma urealyticum, Staphylococcus* species, *Staphylococcus aureus, Enterococcus faecalis, Pasteurella pestis, Campylobacter* species, *Campylobacter jejuni, Treponema* species, *Leptospira* species, *Corynebacterium diphtheria, Hemophilus ducreyi, Hemophilus influenza, Erlichhia* species, among others.

The active antigenic component may also be derived from a fungus or mold such as *Aspergillus floras, Aspergillus fumigatis, Penicillium* species, *Fusarium* species, *Candida* species such as *Candida trichophyton, Candida parapsilosis, Candida glabrata, Candida dubliniensis*, and *Candida albicans, Rhizopus* species, *Cryptococcus* species such as *Cryptococcus neoformans, Cryptococcus grubii, Cryptococcus gattii, Paracoccidiodes brasiliensis, Histoplasma capsulatum*, and other fungi and molds.

The active antigenic component can also be selected from parasitic antigens derived from parasitic species including, but are not limited to *Plasmodium* species, *Trypanosome* species, *Giardia* species, *Boophilus* species, *Babesia* species, *Entamoeba* species, *Eimeria* species, *Leishmania* species, *Schistosoma* species, *Bragia* species, *Fascida* species, *Dirofilaria* species, *Wuchereria* species, *Onchocerea* species, *Treonema* species, *Toxoplasma* species, *Cryptococcus* species, *Coccidia* species, *Histomoniasis* species, *Hexamitiasis* species, *Giardia* species, among others; nematodes including *Ascaris* species, *Trichinella* species, and the like, helminthes such as flukes, tapeworms, among others; and other like pathogenic organisms. Methods for preparing immunogens derived from viruses, bacteria, fungi, molds, protozoa, nematodes, and helminthes are known in the art.

Other useful immunogens can be, for example, purified secreted antigen virulence factors, such as toxins, cytotoxins and the like. Toxin antigens which are detoxified by modifying (toxoids), which can be administered in combination with an adjuvant such as aluminum hydroxide, and can be used to stimulate the formation of toxin-neutralizing antibodies. Examples of toxins that may be used as an immunogen include bacterial endotoxins and exotoxins such as lipopolysaccharide, enterotoxins including heat-labile enterotoxins (LT), heat stable enterotoxins (ST), verotoxin (VT), and the like. Bacterial exotoxin immunogens are secreted into the surrounding medium, and include, for example, diphtheria toxin (*Corynebacterium diptheriae*), tetanus toxin (*Clostridium tetani*), enterotoxins secreted by *Staphylococcus aureus*, botulinum toxins (*Clostridium botulinum*); and toxins produced by algae such as neurotoxins; and the like. Heat-stable endotoxins, released by autolysis of the bacteria, include, for example, cholera toxins released from the grain negative *Vibrio cholerae*, colicins produced by intestinal bacteria such as *E. coli* (bacteriocin).

Immunogens derived from, or originating from viruses, bacteria, fungi and the like may be produced by in vitro culture methods using appropriate culture medium or host cells lines and conventional methods well known to those of ordinary skill in the art. For example, PRRSV may be cultured in an appropriate cell line, such as MA-104 cell line (see U.S. Pat. Nos. 5,587,164; 5,866,401; 5,840,563; 6,251,404 among others). In a similar manner, PCV-2 may be cultured using PK-15 cells line (see U.S. Pat. No. 6,391,314); SIV may be cultured on eggs (U.S. Pat. No. 6,048,537); and *Mycoplasma hyopneumoniae* may be cultured in an appropriate culture medium (U.S. Pat. Nos. 5,968,525; 5,338,543; Ross R. F. et al., (1984) Am. J. Vet. Res, 45: 1899-1905), Advantageously, CDV can be cultured in mink lung cells, such as those described in U.S. Pat. No. 5,178,862. Other techniques for the preparation of virus-derived immunogens are known in the art, and described, for example, in Ulmer et al., Science 259: 1745 (1993); Male et al., Advanced Immunology, pages 14.1-14. 15, J. B. Lippincott Co., Philadelphia, Pa. (1989).

Also useful are antigenic synthetic peptides that mimic antigenic peptide sequences. Such immunogens may be synthesized using a solid-phase technique as described, for example, in R. B. Merrifield, Science 85:2149-2154 (1963), purified, and optionally coupled to a carrier protein such as muramyl dipeptide (MDP), bovine serum albumin (BSA), keyhole limpet hemocyanin (KLH), and the like, using a bifunctional coupling agent such as glutaraldehyde, and the like.

Synthetic antigens are also included within the definition, for example, polyepitopes, flanking epitopes, and other recombinant or synthetically derived antigens. See, e.g., Bergmann et al. (1993) Eur. J. Immunol. 23, 2777-2781; Bergmann et al. (1996) J. Immunol. 157, 3242-3249; Suhrbier A. (1997) Immunol. Cell Biol. 75, 402-408; Gardner et al. (1998) 12th World AIDS Conference, Geneva, Switzerland, Jun. 28-Jul. 3, 1998. Antigenic fragments, for purposes of the present invention, can usually include at least about 3 amino acids, preferably at least about 5 amino acids, more preferably at least about 10-15 amino acids, and most preferably 25 or more amino acids, of the molecule. There is no critical upper limit to the length of the fragment, which could comprise nearly the fall-length protein sequence, or even a fusion protein comprising two or more, or at least one epitope of the protein.

Accordingly, a minimum structure of a nucleic acid expressing an epitope can comprise nucleotides to encode an epitope, immunogen, or antigen of a protein or polyprotein. A nucleic acid encoding a fragment of the total protein or polyprotein, more advantageously, comprises or consists essentially of or consists of a minimum of about 21 nucleotides, advantageously at least about 42 nucleotides, and preferably at least about 57, about 87 or about 150 consecutive or contiguous nucleotides of the sequence encoding the total protein or poly protein. Epitope determination procedures, such as, generating overlapping peptide libraries (Hemmer B. et al., (1998) Immunology Today 19(4), 163-168), Pepscan (Geysen et al. (1984) Proc. Natl. Acad. Sci. USA 81, 3998-4002; Geysen et al., (1985) Proc. Nat. Acad. Sci. USA 82, 178-182; Van der Zee R. et al., (1989) Eur. J. Immunol. 19, 43-47; Geysen H. M., (1990) Southeast Asian J. Trop. Med. Public Health 21, 523-533; Multipin® Peptide Synthesis Kits de Chiron) and algorithms (De Groot A. et al., (1999) Nat. Biotechnol. 17, 533-561), and in PCT Application Serial No. PCT/US2004/022605; all of which are incorporated herein by reference in their entireties can be used in the practice of the invention, without undue experimentation. Other documents cited and incorporated herein may also be consulted for methods for determining epitopes of an immunogen or antigen and thus nucleic acid molecules that encode such epitopes.

Also provided by the invention is a process for producing a freeze-dried stable antigenic composition or vaccine composition comprising, for example, newcastle disease virus, which comprises the step of lyophilizing a stabilized suspension or solution formed by a live attenuated is newcastle disease virus suspension or solution, mixed with a stabilizer according to the invention and a sugar alcohol according to the invention.

"Freeze-drying" or "lyophilization" refers to the process by which a suspension is frozen, after which the water is removed by sublimation at low pressure. As used herein, the term "sublimation" refers to a change in the physical properties of a composition, wherein the composition changes directly from a solid state to a gaseous state without becoming a liquid. As used herein, the "T'g value" is defined as the glass transition temperature, which corresponds to the temperature below which the frozen composition becomes vitreous.

A process for freeze-drying an antigenic suspension or solution according to the invention can comprise the steps of: (a) contacting the antigenic suspension or solution with a stabilizer of the invention, thereby forming a stabilized antigenic suspension or solution; (b) cooling, at atmospheric pressure, the stabilized antigenic suspension or solution to a temperature less than about the T'g value of the stabilized antigenic suspension or solution; (c) drying the stabilized antigenic suspension or solution (i.e., the primary desiccation or sublimation step) by sublimation of ice at to pressure; and (d) removing excess residual water (i.e., secondary drying or desorption step) by further reducing pressure and increasing the temperature of the stabilized antigenic suspension or solution.

The cooling step (b) can occur at temperatures of less than about −40° C. (water freezing step). Drying the stabilized antigenic suspensions or solution by sublimation of ice at low pressure (c) can occur at, for example, pressure lower than or equal to about 200 μbar, whereas a further reduction in pressure can occur at pressures lower than or equal to about 100 μbar. Finally, the temperature of the stabilized antigenic suspension or solution during the removal of excess residual water (d) occurs at, for example, temperatures between about 20° C. and about 30° C.

The process of freeze-drying can also be performed with an antigenic suspension or solution comprising live attenuated newcastle disease virus and at least one active antigenic component derived from a pathogen oilier than a paramyxovirus, which is mixed with a stabilizer according to the invention to obtain a freeze-dried stabilized multivalent antigenic or vaccine composition.

The moisture content of the freeze-dried material can range from about 0.5% to about 5% w/w, preferably from about 0.5% to about 3% w/w, and more preferably from about 1.0% to about 2.6% w/w.

Each step, including water freezing, and its removal during the primary and secondary desiccation, subjects the biological ingredients, such as pathogens, in the antigenic suspensions or solutions of the invention to mechanical, physical and biochemical shock, which have potentially adverse effects upon the structure, appearance, stability, antigenicity, infectivity and viability of the pathogens or biological ingredients.

The stabilizers of the invention allow good stability of live attenuated pathogens like canine paramyxovirus, and maintains the infectivity of, in particular, CDV and cPi2 during the freeze-drying process and during storage. The stability can be calculated by the difference between the infectivity titer before the freeze-drying step, and the infectivity titer after 12 months of storage of the freeze-dried stabilized antigenic composition or vaccine composition at 4° C. Good stability can advantageously comprise a difference of only 1.2 $\log_{10}$, and preferably of only 1.0 $\log_{10}$. Methods for determining the infectivity titer are well known by those skilled in the art. Some methods for determining the infectivity titer are described in the Examples herein. Also, the stability can be estimated by fitting the $\log_{10}$ titer and the time points of the titration during the period of storage using linear regression calculations and/or algorithms.

Further, the stabilizers of the invention allow for freeze-dried pastilles having a good aspect, in other words, having regular form and uniform color. An irregular form can be characterized by the presence of all or a part of the pastille stuck to the bottom of the recipient and remaining immobile after turning over and shearing (stuck aspect). Also, a pastille having a form of a spool (spooled aspect), or separation of the pastille in two parts, following a horizontal plane (de-duplicated aspect), or a pastille having an aspect of a mousse with irregular holes (spongy aspect), or a pastille having the aspect of foam into the recipient (meringue aspect) have an irregular form and are not accepted.

The stabilized freeze-dried antigenic compositions or vaccine compositions using a stabilizer according to the present invention and obtained by the process of freeze-diving described above are encompassed in the present invention.

A further aspect of the present invention provides a kit comprising a first container containing the freeze-dried stabilized antigenic composition or vaccine composition of the invention, and a second contained containing a diluent.

For its use and administration into a subject, the freeze-dried stabilized antigenic composition or vaccine composition can be reconstituted bye rehydration with a diluent. The diluent is typically water, such as demineralized or distilled water, but can also comprise physiological solutions or buffers known in the art.

The reconstituted ready-to-use antigenic compositions or vaccine compositions can be administered to an animal by injection through the parenteral or mucosal route, or preferably by oral or ocular administration by spraying. However, administration of such reconstituted ready-to-use antigenic compositions or vaccine compositions can also comprise intranasal, epicutaneous or topical administration.

The following examples illustrate preparation and potency of the vaccine composition of the present invention when used to immunize a subject against various infectious diseases. Stability evaluations with a titer analysis of a compressed freeze dried tablet form for various vaccine formulations are also presented. The manufacture of the composition of the invention may be made by one or ordinary skill in the art following the teaching in US 2003/0026813 and WO 01/13896, which are incorporated herein in their entirety.

The examples are presented to further illustrate and explain the present invention and should not be taken as limiting in any regard. Unless otherwise indicated in the examples and elsewhere in the specification and claims, all parts and percentages are by weight. Temperatures are in degrees Centigrade.

Stability Studies

The effect of the mannitol on the stability of vaccine compositions was also studied. Six different formulas were made as described in Table 1, to show that the foam controlling agent (mannitol) did not have any negative impact on stability of the formulations at 6 month and 9 month intervals. The tablets made from the formulations were stored at about 5° C. in standard sealed aluminum blister packs for the duration of time before the being reconstituted in diluent and the titers measured. Determination of viral titer of the freeze-dried vaccines was performed by the calculation of the mean titer of three titrations repeated on the same vaccine. The titer results are shown in Table 2.

TABLE 1

| | Formula 1 | Formula 2 | Formula 3 | Formula 4 | Formula 5 | Formula 6 |
|---|---|---|---|---|---|---|
| | Formula for 100 kg | | | | | |
| Freeze dried Antigen and Stabilizer | 30.00 kg | 35.00 kg | 33.00 kg | 40.00 kg | 25.00 kg | 35.00 kg |
| Sodium bicarbonate | 41.02 kg | 28.92 kg | 39.25 kg | 19.50 kg | 43.97 kg | 28.92 kg |
| Mannitol | 0 | 15.00 kg | 0 | 26.00 kg | 0 | 15.00 kg |

TABLE 1-continued

| | Formula 1 | Formula 2 | Formula 3 | Formula 4 | Formula 5 | Formula 6 |
|---|---|---|---|---|---|---|
| Anhydrous citric acid | 28.48 kg | 20.08 kg | 27.25 kg | 13.50 kg | 30.53 kg | 20.08 kg |
| Magnesium stearate | 0.50 kg | 1.00 kg | 0.50 kg | 1.00 kg | 0.50 kg | 1.00 kg |
| Tablet Characteristics | | | | | | |
| Diameter | 12 mm | 12 mm | 15 mm | 15 mm | 12 mm | 12 mm |
| Hardness | 70-200N | 70-200N | 70-200N | 70-200N | 70-200N | 70-200N |
| Weight (g) | 0.74-0.90 | 0.63-0.77 | 1.10-1.34 | 0.90-1.10 | 0.74-0.90 | 0.527-0.645 |
| Thickness (mm) | 4.5-4.9 | <5 | 4.5-4.9 | <5 | 4.5-4.9 | 3.5-3.9 |

TABLE 2

| Titer Results: | | | | | | |
|---|---|---|---|---|---|---|
| Formula # | Antigen | Stabilizer | MeanTiter (0 months) | MeanTiter (3 months) | MeanTiter (6 months) | MeanTiter (9 months) |
| 1 | Newcastle Disease virus strain VG/GA | Protein hydrolysate Potassium glutamate Bovine albumin | 9.4 | 9.0 | 9.0 | 9.1 |
| 2 | Newcastle Disease virus strain VG/GA | Protein hydrolysate Potassium glutamate Bovine albumin | 9.5 | 9.3 | 9.2 | 9.4 |
| 3 | Infectious Bronchitis virus strain CR88121 | Protein hydrolysate | 7.6 | 7.1 | 7.3 | 7.0 |
| 4 | Infectious Bronchitis virus strain CR88121 | Protein hydrolysate | 7.9 | 7.8 | 7.8 | 7.8 |
| 5 | Infectious Bronchitis virus strain H120 | Protein hydrolysate | 9.4 | 7.1 | 7.4 | — |
| 6 | Infectious Bronchitis virus strain H120 | Protein hydrolysate | 7.5 | 7.6 | 7.7 | — |

Units of Titer: Log10 DICC50/cp

The results show very good stability of the formulations containing mannitol for a long storage period at 5° C.

Foam Controlling Studies a) Concentrations of Foam Controlling Agent:

Three formulations were made as shown in Table 3 to examine the effect of the amount of foam controlling agent on reducing foaming in solution. These formulations were tableted using conventional means for making effervescent tablets. The tablets were mixed in water at room temperature and the foaming measured at the peak foaming. The sodium bicarbonate and citric acid act as an effervescent agent to help mix the composition in the water. The results shown in FIG. 1 show that Formula II (containing 15% mannitol), and Formula III, (containing 33% mannitol), have less foam forming than the Formula I (control containing 0% mannitol). This shows the decrease in foam formation as the amount of mannitol increases in the composition.

TABLE 3

Figure 2:
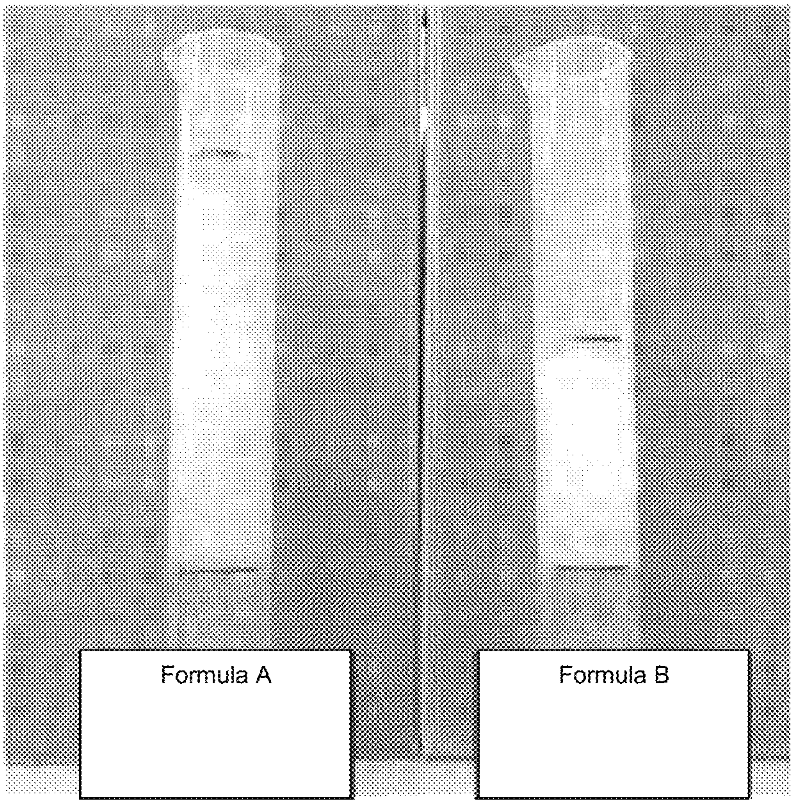
FIG. 2 shows containers containing Formula A (containing 0% mannitol) and Formula B (containing 15% mannitol).
Figure 3:
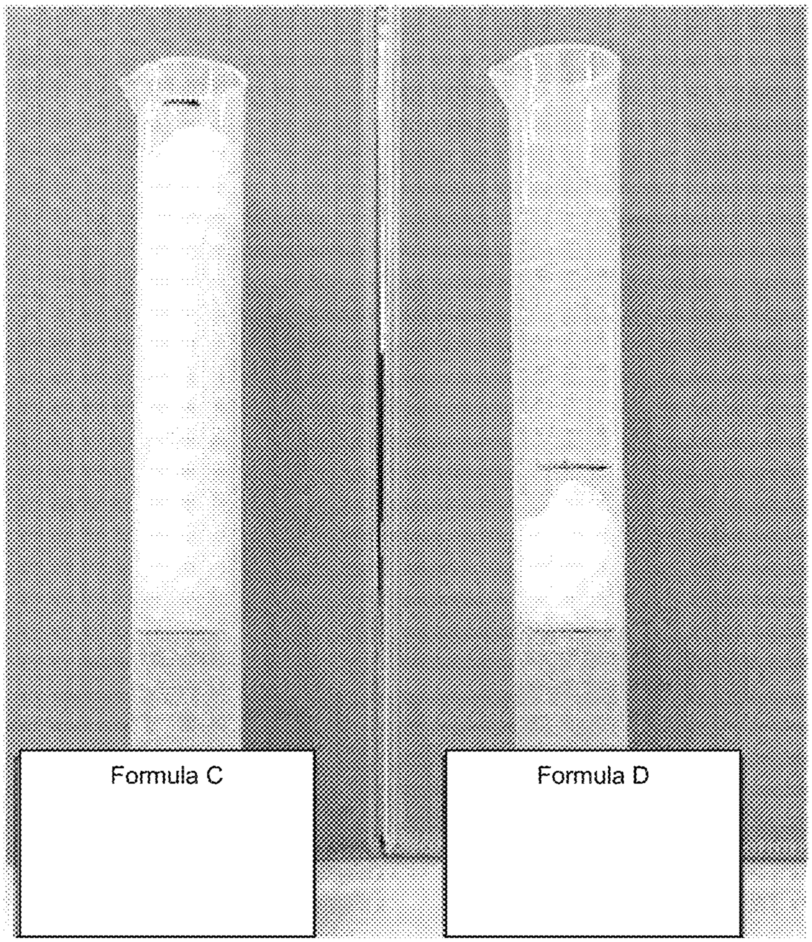
FIG. 3 shows containers containing Formula C (containing 0% mannitol) and Formula D (containing 15% mannitol).
Figure 4:
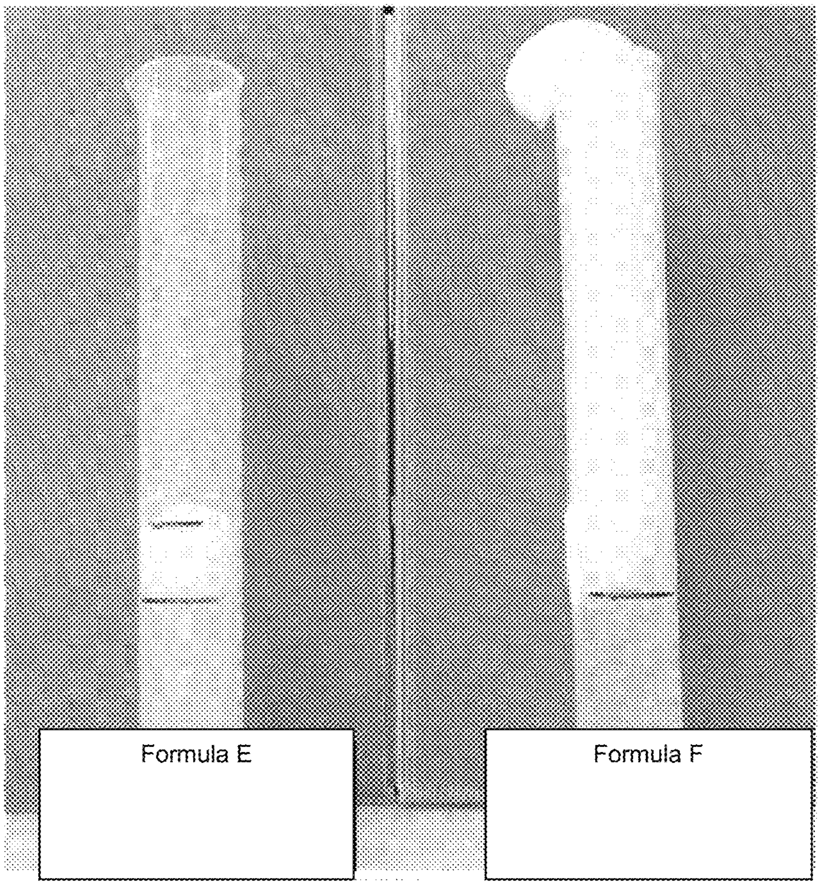
FIG. 4 shows containers containing Formula E (containing 26% mannitol) and Formula F (containing 0% mannitol).

| Composition | Formula I | Formula II | Formula III |
|---|---|---|---|
| Placebo and Stabilizer | 33% | 33% | 33% |
| Sodium bicarbonate and Anhydrous citric acid | 66% | 51% | 33% |
| Mannitol | 0% | 15% | 33% |
| Magnesium stearate | 1% | 1% | 1% |

b) Examination of the Effect of Mannitol on Different Vaccine Compositions:

Six vaccine compositions were made as shown in Table 4. These compositions were tableted using conventional means for making effervescent tablets. The tablets were mixed in water at room temperature and the foaming measured at the peak laming. The sodium bicarbonate and citric acid act as an effervescent agent to help mix the compositor in the water. The results shown in FIG. 2 show that Formula B (containing 15% mannitol) has about 50% less foam than Formula A (Containing 0% mannitol). FIG. 3 shows that Formula D (containing 15% mannitol) has about 60% less foam than Formula C (containing 0% mannitol). FIG. 4 shows that Formula E (containing 26% mannitol) has about 80% less forming than Formula F (containing 0% mannitol).

TABLE 4

| Composition | Formula A | Formula B | Formula C | Formula D | Formula E | Formula F |
|---|---|---|---|---|---|---|
| Freeze dried Antigen and Stabilizer | Newcastle Disease virus strain VG/GA (30%) | Newcastle Disease virus strain VG/GA (35%) | Infectious Bronchitis virus stain H120 (25%) | Infectious Bronchitis virus strain H120 (35%) | Infectious Bronchitis virus strain CR88121 (40%) | Infectious Bronchitis virus strain CR88121 (33%) |
| Sodium bicarbonate Anhydrous citric acid | 69% | 49% | 74% | 49% | 33% | 66 |
| Mannitol | 0% | 15% | 0% | 15% | 26% | 0% |
| Magnesium stearate | 1% | 1% | 1% | 1% | 1% | 1% |

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed:

1. A method of making a solid vaccine composition having reduced foaming when mixed with a liquid diluent, the method comprises mixing an effective amount of a foam controlling agent with at least one anhydrous antigenic component, a stabilizer, and an effervescent agent;

wherein the foam controlling agent is a sugar alcohol, wherein the effective amount of sugar alcohol is about 15% to 40% by weight of the solid vaccine composition, and upon adding a diluent to the solid vaccine composition, the effervescent agent reacts to form gas in situ, and foam resulting from the gas is reduced.

2. The method according to claim 1, wherein the method further comprises:

compressing the solid vaccine composition to form a compressed vaccine composition.

3. The method according to claim 1, wherein the at least one anhydrous antigenic component is lyophilized or dried.

4. The method according to claim 1, wherein the stabilizer comprises one or more amino acid or salts thereof, protein or salts thereof, albumin, gelatin, or combinations thereof.

5. The method according to claim 1, wherein the at least one anhydrous antigenic component is newcastle disease virus, infectious bronchitis virus, fowl pox virus, avian encephalomyelitis virus, marek's disease virus, *Trichophyton verrucosum*, avian paramyxovirus, *mycobacterium* paratuberculosis, meleagrid herpesvirus, orf virus, or sheep pox virus.

6. The method according to claim 1, wherein the at least one anhydrous antigenic component is newcastle disease virus or infectious bronchitis virus.

7. The method according to claim 1, wherein the diluent is water, and upon dissolution of the composition, an effervescent reaction occurs and gas is formed in situ.

8. The method according to claim 1, wherein the composition comprises a pair of effervescent agents.

9. The method according to claim 8, wherein the pair of effervescent agents comprises a salt and an acid.

10. The method according to claim 9, wherein the acid is citric acid, tartaric acid, malic acid, fumaric acid, adipic acid, succinic acid, acid anhydrides or mixtures thereof.

11. The method according to claim 9, wherein the salt is carbonate salts, bicarbonate salts, sesquicarbonate salts, or mixtures thereof.

12. The method according to claim 1, wherein the effective amount of sugar alcohol is about 33% to 40% by weight of the composition.

13. The method according to claim 1, wherein the effective amount of sugar alcohol is about 26% to 35% by weight of the composition.

14. The method according to claim 1, wherein the effective amount of sugar alcohol is about 25% to 33% by weight of the composition.

15. The method according to claim 1, wherein the effective amount of sugar alcohol is about 25% to 40% by weight of the composition.

16. The method according to claim 1, wherein the at least one anhydrous antigenic component is about 20% to about 50% by weight of the composition.

17. The method according to claim 1, wherein anhydrous antigenic component is up about 20% to about 40% by weight of the composition.

18. The method according to claim 1, wherein the solid vaccine composition is characterized by complete dissolution of the composition in the diluent between about 60 and 700 seconds upon contact with the diluent.

19. The method according to claim 1, wherein the solid vaccine composition is characterized by complete dissolution of the composition in the diluent between about 60 and 300 seconds upon contact with the diluent.

20. The method according to claim 1, wherein the foaming of the solid vaccine composition is reduced relative to the foaming of the composition in the absence of the sugar alcohol.

21. The method according to claim 1, wherein the sugar alcohol is xylitol, mannitol, sorbitol or a mixture thereof.

22. A method of making a stable solid vaccine composition having reduced foaming when mixed with an aqueous liquid diluent, said foaming formed by carbon dioxide gas in situ by reaction of an effervescent agent contained in the stable solid vaccine composition with the aqueous liquid diluent, said stable solid vaccine composition comprising:

an anhydrous antigenic component comprising an antigen, a stabilizer, said stabilizer comprising one or more amino acid or salts thereof, protein or salts thereof, albumin, gelatin, or combinations thereof that gives rise to foaming when the composition is mixed with the aqueous liquid diluent; and the effervescent agent, said effervescent agent comprising an effervescent pair that during dissolution in water reacts and generates carbon dioxide, said method comprising including in the stable solid vaccine composition an effective amount of a foam controlling agent comprising a sugar alcohol comprising xylitol, mannitol, sorbitol or a mixture thereof; and wherein the effervescent pair comprises:

(a) an acidic component, said acid component comprising citric acid, adipic acid, tartaric acid, maleic acid, boric acid, benzoic acid, hydroxybenzoic acid, methoxybenzoic acid, mandelic acid, malonic acid, lactic acid, pyruvic acid, glutaric acid, aspartic acid, hydrochloric acid, oxalic acid, salicylic acid, succinic acid, or acetic acid; or said acid component comprising citric acid, tartaric acid, malic acid, fumaric acid, adipic acid, succinic acid, acid anhydrides or mixtures thereof and (b) a basic component, said basic component comprising sodium carbonate, sodium bicarbonate, glycine carbonate, potassium carbonate, potassium bicarbonate, potassium dihydrogen citrate, or calcium carbonate, wherein:

the effective amount of sugar alcohol is 25% to 40% by weight of the stable solid vaccine composition, and the antigen comprises Newcastle disease virus, infectious bronchitis virus, avian smallpox virus, avian encephalomyelitis virus, disease virus Marek, *Trichophyton verrucosum*, avian paramyxovirus, *mycobacterium* paratuberculosis, herpesvirus meleagrid, orf virus, or sheep pox virus, and dissolution of the stable solid vaccine composition in the aqueous liquid diluent results in the effervescent agent reacting and forming carbon dioxide gas in situ with reduced foaming relative to foaming by a composition comprising the anhydrous antigenic component and the effervescent agent and having an absence of the effective amount of the sugar alcohol.

23. The method of claim 22, wherein the anhydrous antigen component is lyophilized or dried.

24. The process of claim 22, further comprising compressing the stable solid vaccine composition into a tablet.

25. The method of claim 22, wherein the stabilizer comprises albumin.

26. The method of claim 22, wherein the antigen comprises Newcastle disease virus or infectious bronchitis virus.

27. The method of claim 26, wherein the antigen comprises infectious bronchitis virus strain CR88121, or H120 Infectious Bronchitis virus strain or the antigen comprises Newcastle Disease virus strain VG/GA.

28. A method of making a stable solid vaccine composition having reduced foaming when mixed with an aqueous liquid diluent, said foaming formed by carbon dioxide gas in situ by reaction of an effervescent agent contained in the stable solid vaccine composition with the aqueous liquid diluent, said stable solid vaccine composition comprising:

an anhydrous antigenic component comprising an antigen, a stabilizer, said stabilizer comprising one or more amino acid or salts thereof, protein or salts thereof, albumin, gelatin, or combinations thereof that gives rise to foaming when the composition is mixed with aqueous liquid diluent; and the effervescent agent, said effervescent agent comprising an effervescent pair that during dissolution in water reacts and generates carbon dioxide, said method comprising including in the stable solid vaccine composition an effective amount of a foam controlling agent comprising a sugar alcohol comprising xylitol, mannitol, sorbitol or a mixture thereof; and wherein the effervescent pair comprises:

(a) an acidic component, said acid component comprising citric acid, adipic acid, tartaric acid, maleic acid, boric acid, benzoic acid, hydroxybenzoic acid, methoxybenzoic acid, mandelic acid, malonic acid, lactic acid, pyruvic acid, glutaric acid, aspartic acid, hydrochloric acid, oxalic acid, salicylic acid, succinic acid, or acetic acid; or said acid component comprising citric acid, tartaric acid, malic acid, fumaric acid, adipic acid, succinic acid, acid anhydrides or mixtures thereof and and (b) a basic component, said basic component comprising sodium carbonate, sodium bicarbonate, glycine carbonate, potassium carbonate, potassium bicarbonate, potassium dihydrogen citrate, or calcium carbonate, wherein:

the effective amount of sugar alcohol is 25% to 40% by weight of the stable solid vaccine composition, and dissolution of the stable solid vaccine composition in the aqueous liquid diluent results in the effervescent agent reacting and forming carbon dioxide gas in situ with reduced foaming relative to foaming by a composition comprising the anhydrous antigenic component and the effervescent agent but having an absence of the effective amount of the sugar alcohol.

29. The method according to claim 28, wherein the antigen comprises Newcastle disease virus, infectious bronchitis virus, avian smallpox virus, avian encephalomyelitis virus, Marek's disease, *Trichophyton verrucosum*, avian paramyxovirus, *mycobacterium* paratuberculosis, herpesvirus meleagrid, orf virus, or sheep pox virus.

30. The method according claim 22 or 28, wherein the effective amount of sugar alcohol is between 33% and 40% by weight of the stable solid vaccine composition.

31. The method according claim 22 or 28, wherein the effective amount of sugar alcohol is between 26% and 35% by weight of the stable solid vaccine composition.

32. The method according claim 22 or 28, wherein the effective amount of sugar alcohol is between 25% and 33% by weight of the stable solid vaccine composition.

33. The method according claim 22 or 28, wherein the anhydrous antigen component is about 10% to about 50% by weight of the composition.

34. The method according claim 22 or 28, wherein the anhydrous antigen component is about 20% to about 40% by weight of the composition.

35. The method according claim 22 or 28, wherein the dissolution occurs between 60 and 700 seconds after contact with the aqueous liquid diluent.

36. The method according claim 22 or 28, wherein sugar alcohol comprises mannitol.

37. The method according claim 22 or 28, wherein the composition has a friability of less than 2%.

38. The method according claim 22 or 28, wherein the antigen comprises a live virus and the stable solid vaccine composition additionally comprises neutralizing antibodies against the virus.

39. The method according claim 22 or 28, wherein the stable solid vaccine composition is stable at 5° C. under anhydrous conditions for at least 9 months.

40. The method according claim 22 or 28, wherein the stable solid vaccine composition comprises (i) mannitol in an amount of 25%, 26%, 33% or 40% by weight of the stable solid vaccine composition, (ii) sodium bicarbonate and citric acid in an amount of 33%, 49% or 51% by weight of the stable solid vaccine composition, and (iii) magnesium stearate in an amount of 1% by weight of the stable solid vaccine composition.

41. The method according claim 22 or 28, wherein the basic component comprises sodium bicarbonate.

42. The method according claim 22 or 28, wherein the acidic component comprises citric acid.

43. The method according claim 22 or 28, wherein dissolution of the stable solid vaccine composition in the aqueous liquid diluent also results in carbonic acid being formed.

44. The method according claim 42, wherein the sugar alcohol comprises mannitol.

45. The method according to claim 44, wherein the basic component comprises sodium bicarbonate.

46. A method of making a stable solid vaccine composition having reduced foaming when mixed with an aqueous liquid diluent, said foaming formed by carbon dioxide gas in situ by reaction of an effervescent agent contained in the stable solid vaccine composition with the aqueous liquid diluent, said stable solid vaccine composition comprising:

an anhydrous antigenic component comprising an antigen, a stabilizer, said stabilizer comprising one or more amino acid or salts thereof, protein or salts thereof, albumin, gelatin, or combinations thereof that gives rise to foaming when the composition is mixed with aqueous liquid diluent; and the effervescent agent, said effervescent agent comprising an effervescent pair that during dissolution in water reacts and generates carbon dioxide, said method comprising including in the stable solid vaccine composition an effective amount of a foam controlling agent comprising a sugar alcohol comprising xylitol, mannitol, sorbitol or a mixture thereof; and wherein the effervescent pair comprises:

(a) an acidic component, said acid component comprising citric acid, adipic acid, tartaric acid, maleic acid, boric acid, benzoic acid, hydroxybenzoic acid, methoxybenzoic acid, mandelic acid, malonic acid, lactic acid, pyruvic acid, glutaric acid, aspartic acid, hydrochloric acid, oxalic acid, salicylic acid, succinic acid, or acetic acid; or said acid component comprising citric acid, tartaric acid, malic acid, fumaric acid, adipic acid, succinic acid, acid anhydrides or mixtures thereof and and (b) a basic component, said basic component comprising sodium carbonate, sodium bicarbonate, glycine carbonate, potassium carbonate, potassium bicarbonate, potassium dihydrogen citrate, or calcium carbonate, wherein:

the effective amount of sugar alcohol is 15% to 40% by weight of the stable solid vaccine composition, and the antigen comprises Newcastle disease virus, infectious bronchitis virus, avian smallpox virus, avian encephalomyelitis virus, disease virus Marek, *Trichophyton verrucosum*, avian paramyxovirus, *mycobacterium* paratuberculosis, herpesvirus meleagrid, orf virus, or sheep pox virus, and dissolution of the stable solid vaccine composition in the aqueous liquid diluent results in the effervescent agent reacting and forming carbon dioxide gas in situ with reduced foaming relative to foaming by a composition comprising the anhydrous antigenic component and the effervescent agent but having an absence of the effective amount of the sugar alcohol.

* * * * *